(12) United States Patent
Adams

(10) Patent No.: US 10,709,882 B2
(45) Date of Patent: Jul. 14, 2020

(54) THERAPEUTIC AGENT DELIVERY APPARATUS AND PROCESS

(75) Inventor: Kenneth W. Adams, North York (CA)

(73) Assignee: KENNETH ADAMS MEDICINE PROFESSIONAL CORPORATION, Toronto, ON (CA)

( * ) Notice: Subject to any disclaimer, the term of this patent is extended or adjusted under 35 U.S.C. 154(b) by 714 days.

(21) Appl. No.: 13/519,909

(22) PCT Filed: Dec. 3, 2010

(86) PCT No.: PCT/CA2010/001924
§ 371 (c)(1),
(2), (4) Date: Jun. 29, 2012

(87) PCT Pub. No.: WO2011/079372
PCT Pub. Date: Jul. 7, 2011

(65) Prior Publication Data
US 2012/0283186 A1    Nov. 8, 2012

(30) Foreign Application Priority Data
Dec. 30, 2009   (CA) ..................................... 2689400

(51) Int. Cl.
*A61M 37/00* (2006.01)
*A61M 5/31* (2006.01)
*A61M 5/142* (2006.01)
*A61M 5/178* (2006.01)

(52) U.S. Cl.
CPC ............ *A61M 37/00* (2013.01); *A61M 5/142* (2013.01); *A61M 5/178* (2013.01); *A61M 5/31* (2013.01)

(58) Field of Classification Search
CPC .. A61M 5/1407; A61M 5/1408; A61M 5/142; A61M 5/3295; A61M 5/14244; A61M 5/3298; A61M 5/16827; A61M 5/19; A61M 5/31596; A61M 2205/31598; A61M 5/00; A61M 5/14; A61M 5/178; A61M 5/20; A61M 5/145; A61M 5/1452; A61M 2005/14533; A61M 37/00; A61M 5/31
USPC ........................................................ 604/500
See application file for complete search history.

(56) References Cited

U.S. PATENT DOCUMENTS

| | | | | |
|---|---|---|---|---|
| 4,256,153 A | * | 3/1981 | Lamaziere | ............ B01L 3/0227 141/238 |
| 4,286,592 A | * | 9/1981 | Chandrasekaran | ......................... A61F 13/00063 424/448 |
| 4,756,706 A | * | 7/1988 | Kerns | ................. A61M 5/1413 128/DIG. 13 |

(Continued)

Primary Examiner — Jason E Flick
(74) Attorney, Agent, or Firm — Jeffrey S. Melcher; Melcher Patent Law PLLC

(57) ABSTRACT

A method and device to deliver medication in a liquid, gel or suspension formulation to a plurality of adjacent tissue sites of a mammal, the device comprising a plurality of tissue-engaging members for receiving the medication and operably engageable with the plurality of tissue sites; means for supplying the tissue-engaging members with the formulation, and to temporarily sustain and control the rate of therapeutic agent/unit of time and preferably to sustain these controlled delivery rates over extended periods of time to enhance the local therapeutic effect of these therapeutic agents and to reduce the systemic toxicity and reduce unwanted side effects.

9 Claims, 3 Drawing Sheets

(56) References Cited

U.S. PATENT DOCUMENTS

| | | | | |
|---|---|---|---|---|
| 5,154,181 A * | 10/1992 | Fishman | A61B 17/205 | 600/556 |
| 6,428,504 B1 * | 8/2002 | Riaziat | A61N 1/327 | 604/65 |
| 6,468,247 B1 * | 10/2002 | Zamoyski | A61M 5/1408 | 604/131 |
| 6,551,290 B1 * | 4/2003 | Elsberry | A61M 25/0069 | 604/173 |
| 6,611,707 B1 * | 8/2003 | Prausnitz | A61B 5/1411 | 604/21 |
| 2002/0107502 A1 * | 8/2002 | Hung | A61B 10/0045 | 604/506 |
| 2004/0254527 A1 * | 12/2004 | Vitello | A61M 15/025 | 604/82 |
| 2005/0203464 A1 * | 9/2005 | Haider | A61M 5/19 | 604/191 |
| 2006/0079846 A1 * | 4/2006 | Williams | A61M 5/002 | 604/191 |
| 2007/0088271 A1 * | 4/2007 | Richards | A61M 5/14244 | 604/151 |
| 2007/0239099 A1 * | 10/2007 | Goldfarb | A61N 1/327 | 604/20 |
| 2008/0287864 A1 * | 11/2008 | Rosenberg | A61B 17/205 | 604/60 |
| 2009/0030373 A1 * | 1/2009 | Gill | A61M 39/0208 | 604/151 |
| 2009/0240232 A1 * | 9/2009 | Gonnelli | A61M 5/14526 | 604/506 |
| 2010/0145303 A1 * | 6/2010 | Yodfat | A61M 5/1408 | 604/506 |
| 2010/0330589 A1 * | 12/2010 | Bahrami | A61M 5/1452 | 435/7.9 |
| 2014/0114279 A1 * | 4/2014 | Klinghoffer | A61M 5/1408 | 604/506 |

* cited by examiner

THERAPEUTIC AGENT DELIVERY APPARATUS AND PROCESS

FIELD OF THE INVENTION

The invention relates to apparatus and method of delivering therapeutic agents to a mammal and more particularly, for delivery to a plurality of 2-D or 3-D array of spatially adjacent tissue sites to produce therapeutic levels throughout a plurality of adjacent specific therapeutic sites or plurality of specific volumes of tissue to efficiently maintain elevated therapeutic concentrations in the therapeutic region with dramatic reductions in the amounts of therapeutic agent administered during the temporal period of action of the therapeutic agent.

BACKGROUND OF THE INVENTION

Often, potentially effective biologic agents that demonstrate efficacy in preliminary research and testing will fail to be clinically useful when tested in clinical trials. It has been the observation of the inventor that many therapeutic agents have failed to yield a significant clinical response, even when the maximum dosage is utilized because of inefficient or ineffective modes of administration.

Under some circumstances, a medicine may be effective, but only at dosage levels that may cause toxicity. Often these undesirable side effects occur in tissues that are in sites distant to the intended site of action. Lowering the dose to non-toxic levels renders the drug ineffective with the standard methods of oral or parenteral administration. Even in the absence of toxicity therapeutic agents that have been shown to have effects on specific receptors often fail to yield any therapeutic clinical response in studies on living animals.

There are many examples of medications and treatments with biological agents that theoretically work in vivo, but show no significant effect when applied in vitro.

The systemic application of therapeutic agents to produce therapeutic effects in localized tissues is inefficient and dramatically increases the potential toxicity while limiting the potential effectiveness of the therapeutic agent.

It is a basic principle of pharmacokinetics that in order for a drug or therapeutic agent to be effective, it must be present in an appropriate concentration for an appropriate duration of time. If it does not reach an adequate concentration it cannot be effective. Even if it does reach a therapeutic concentration, if the therapeutic concentration is of too short duration the effect may not be clinically detectable.

The inventor has discovered that the systemic application of therapeutic agent(s) frequently fails to achieve a clinically significant effect for the simple reason that the drug or therapeutic agent is not present in an adequate concentration for an adequate duration of time. Due to regional variations in blood flow, medications and therapeutic agents may not be distributed homogeneously through the volume of tissue being treated in an adequate concentration for an appropriate duration of time. For example, to reach dense avascular structures such as tendons, ligaments, areas that have reduced vascular supplies such as infacted and devascularized tissues or regions of scarring and cirrhosis, regional areas that are naturally avascular such as tumors that have out grown their blood supply, or regions that have been traumatized by chemical, mechanical or thermal injury requires a dramatic increase in the size and frequency of systemically administered therapeutic agents in order to achieve an adequate therapeutic effect in those regions.

These factors affecting the heterogeneously variable concentration of therapeutic agents by various routes and methods of administering these agents are especially amplified when trying to systemically deliver therapeutic agents with relatively toxic therapeutic agents(=low therapeutic) index to areas with relatively limited perfusion, penetration or limited solubility.

For example, while the brain, heart, liver and kidneys receive a disproportionately high rate of blood flow (at rest the brain is 2% body weight and receives 25% of resting cardiac output, the kidney is 0.5% body weight and receives 20% of resting cardiac output, and the liver is 3% body weight and receives 15% of resting cardiac output and these vital organs will be subjected to increased toxicity. As well the gut and subsequently the liver also have a very disproportionate high level of blood supply immediately following any meal. As a result these essential organs are often the site of serious life threatening toxicity. Other therapeutic agent may exhibit very specific idiosyncratic reactions to these or other tissues such as the bone marrow. A therapeutic delivery device that could dramatically increase the effectiveness of a therapeutic agent(s) while reducing the total dose administered to achieve therapeutic levels by magnitudes of order would simultaneously increase effectiveness while dramatically reducing toxicity.

Even when medications are applied locally they can often fail to reach the intended site of action. In clinical situations where medications are self administered topically or by injection they will rarely be administered in frequencies of more than two to three times a day. And when medications are being administered parenterally in outpatient situations by health professionals, the dosing intervals may be even less frequent.

When patients or health professionals inject medications locally, the rate of injection is so rapid (when compared to the invention) it will not allow the medication to flow through the intercellular spaces but instead will result dissection through tissue plane resulting in isolated pockets of medication. When the therapeutic agent delivery device is used the rate of infusion can be titrated to the tissue site to ensure that the minimal flow rate can be used to yield this type of intercellular dispersion that avoids tissue dissection. This inventor asserts that this type of dispersion is magnitude of order faster than diffusion and requires magnitudes of order less medication being injected per unit of time in a much more uniform pattern of distribution. This contrasts with conventional local injections where the high rate of injection of relatively large volumes over short periods of time will dissect the tissue and leave localized pockets of medication with a much more uneven distribution.

And when the therapeutic agent delivery device is compared to systemic injections there is a even more dramatic reduction in the amount of therapeutic agent that will need to be administered by the therapeutic agent delivery device to achieve an equivalent therapeutic effect. This device can deliver medication to a plurality of topical sites for some clinical applications, or may require a plurality of parenteral delivery sites for other clinical applications.

This invention, as proposed for parenterally applied medication, will provide a controlled rate of volume per unit of time to a plurality of being delivered by slow continuous or frequent small intermittent infusions through a plurality of injection sites to produce a sustained and relatively continuous pressure gradient to allow continuous flow of the therapeutic agent through the intercellular and intermolecular tissue spaces which will effectively produce a more homogeneous dispersion of the therapeutic agent through a much larger volume of tissue. This much larger volume of distribution will dramatically improve the local diffusion and vascular redistribution to achieve much more uniform therapeutic levels between the plurality of therapeutic sites utilized by this invention.

Current state of art is to apply medications as individual doses through all possible routes of administration such as parenteral/injectable, inhalation, intranasal, sublingual, oral, rectal, or topical. Pharmakinetic studies are done by those skilled in the art to establish the highest safe dose, and then various lower doses are tested to establish the lowest optimal effective dose generally with the lowest risk of side-effects and/or toxicity.

Even through infusion pumps may be used, e.g. diabetes, or to inject intravenous medications at precisely controlled rate, e.g. morphine, for pain relief by IV drip, Syntocinon drip for induction of labor, these are medications applied at a distant site to deliver a $R_x$ agent for a localized tissue effect that is distant for the site of intravenous infusion.

These various methods of delivering biological active agents fail if the agent cannot achieve and/or sustain an appropriately effective concentration at its intended site of action or if it induces unacceptable side effects.

Even though a medication may produce significant serum (venous) levels, actual tissue levels are in most clinical applications never tested. Even though tissue levels are assumed to closely approximate serum levels, in fact, many factors, from variations in regional blood flow and regional diffusion rate, distance the agent must diffuse to reach the site of action. These (multitude of factors; alone or in combination) may completely and/or functionally prevent the biological and/or pharmacological agent from acting effectively at the site of action.

There, thus, remains a need for a more efficacious method of delivering therapeutic agents to the desired site of action under many differing clinical situations.

SUMMARY OF THE INVENTION

A therapeutic agent can only be effective when it is present in the appropriate concentration for the appropriate length of time at the desired site of action.

This invention improves the local therapeutic effect of any medication or therapeutic agent by many magnitudes of order over all existing medication delivery systems by:
1. Maximizing and sustaining the duration of effective therapeutic concentrations at the desired site of local action.
2. Producing sustained local pressures to a plurality of therapeutic delivery sites to convect or drive solutions of therapeutic agents through the microscopic intercellular and intermolecular tissue spaces, at rates that are much faster than diffusion.
3. This convection induced by sustained pressure dramatically reduces the distance that therapeutic agents must diffuse in order to achieve therapeutic concentrations in regions with low solubility or low vascularity.
4. By maintaining prolonged high concentration gradients around avascular regions this device allows the slow process of diffusion to penetrate deeply and evenly to become therapeutic in a way that is impossible for intermittent dosing by any other traditional routes of administration to achieve. This is particularly relevant for relatively avascular structures or relatively avascular tissue areas that require treatment.
5. By sustaining prolonged and consistent delivery of therapeutic agents to a plurality of adjacent tissue sites, this invention allows diffusion to effectively equilibrate and achieve much more homogeneous tissue levels throughout the entire volume of tissue being treated by the plurality of tissue delivery sites when compared to by any existing medical devices or traditional administration techniques.

In one aspect, the present invention is directed to a multi-lumen non-vascular medical device which provides a more uniform and thus more effective delivery of fluids containing drugs or therapeutic agents to a desired localized tissue or areas of local action. The present invention relates to a therapeutic agent delivery system and device that locally delivers a therapeutic agent(s) to a plurality of spatially adjacent tissue sites to maintain continuous localized therapeutic levels of a therapeutic agent(s) over a prolonged period.

For example, if treating localized fibrous regions such as the plaques that occur in Peyronie's disease in the penis, the volume of distribution of these plaques compared to the rest of the body or systemic volume of distribution could be 1,000-100,000 to 1 ($\Delta 10^{3-5}$).

Due to variations in regional blood flow, during stress, dehydration or chronically in some erectile dysfunction, there can be dramatic reduction in blood flow to the penis from peak flows <1 cm$^3$/sec to high flow situations of 100 cm/sec from the multiple arterial inputs ($\Delta 10^{0-2}$).

In Peyronie's disease the associated plaques are dense avascular areas inside of the penis. In these plaques, therapeutic agents can only penetrate by diffusing very long distances. With intermittent dosing, the penetration of a single systemic doses will be many magnitudes of order lower inside the plaque as opposed to tissues adjacent to vascular structures. Estimated effect is $10^8$ since the time for diffusion varies inversely with the square of the distance. Estimate one micron for tissues adjacent to capillaries versus one centimeter=10,000 microns. 10,000 squared is one hundred million=$10^8$.

These factors alone may potentially increase the levels of a locally applied therapeutic agent by up to $10^{3-5} \cdot 10^{0-2} \cdot 10^8 = 10^{11-15} = 10^{11}$ to $10^{15}$.

Then the time factor must be considered. An intravenous bolus may only produce high serum levels for a few minutes versus prolonged continuous local application. Assuming 15 minutes out of 24 hours, $$60 \times 24/15 = 1440/15 = 436/1 = 4.36 \times 10^2 = 10^{2.4}.$$

The resulting product $10^{11-15} \cdot 10^{2.4} = 10^{13.4} - 10^{17.4}$ stronger therapeutic effect of a single continuous local application by the invention versus a single daily bolus intravenous infusion of the same amount of a therapeutic agent inside of a penile plaque or other dense and relatively avascular structures in the therapeutic area. This means that a trillion× billion less medication may be as effective as a single intravenous injection.

Although the therapeutic agent may often be delivered intravascularly to reach the non-vascular sites of action of the therapeutic agent(s), in preferred embodiments the therapeutic agent is delivered, preferably, to the intercellular compartment. However, it will be understood by those skilled in the art that inadvertent intravascular injection in some of the sites will be unavoidable when a relatively large number of sites are used. But the slow controlled rate of flow to each region or area produced by this invention will result in the majority of sites maintaining a maximum therapeutic effect. As a result the agent will tend to flow evenly into the plurality of injection site through the interstitial spaces as it concurrently will diffuse and disperse into the adjacent intracellular and intravascular spaces.

This contrasts with the effect of one or more sites penetrating a blood vessel when a plurality of sites are supplied by other multi-luminal therapeutic agent delivery devices that have a common pressure or common source. With these types of devices or tissue pumps are utilized any intravascular site will have resistance many times smaller than the majority of sites and result in the bulk of the flow going into that vessel. Very little therapeutic agent will flow to the adjacent non-vascular sites and the effect will tend to approximate an intravenous/systemic administration. This will dramatically reduces the flow to the other non-vascular sites due to the relatively high resistance in these sites causing the bulk of the therapeutic site being non-therapeutic or at best only marginally therapeutic. And even if none of the plurality of sites become intravascular the variability of resistance that occurs between sites will mean that these different sites will receive different flow rates and an uneven delivery of therapeutic agent. These two points illustrate some of the major advantages of the therapeutic agent delivery device described in this invention which controls the flow rate to multiple different sites to eliminate the variability in flow rate that occurs with variability in the resistance to flow at different sites.

Even in relatively homogeneous tissues there will be large variations in resistance when pluralities of injection sites are used to deliver a therapeutic agent. And these differences become even more significant in tissues that are more heterogeneous in terms of the resistance to flow.

The therapeutic agent delivery system and devices according to the invention comprise or are adapted to be connected to a single, or preferably to a plurality of different liquid or gel sources, preferably, including a plurality of independent and non-communicating fluid conveying lumens.

The lumens or chambers of use in the practise of the invention transmit the therapeutic agent(s) to a plurality of adjacent spatially or topically related sites each of which may be housed separately. In alternative embodiments, the lumen or chambers are joined in a series of groupings, or formed in a single catheter. However, at the tissue site of delivery they must individually release the therapeutic agent(s) to a plurality of adjacent spatially or topically related sites.

In alternative embodiments, different mechanical means are used to correctly orient, direct and stabilize the sites of application. For example, application of a device according to a penis is different from applications to a tendon or internal organs, localized tumors or a localized pathological lesion(s) in a variety of different tissues.

The plurality of adjacent spatially or topically related sites in some therapeutic/clinical applications requires that the therapeutic agent(s) are released topically onto a plurality of sites on the skin or surface of a body part or organ to achieve a successful therapeutic outcome.

In other applications, optimal delivery of the therapeutic agent is accessed by a plurality of adjacent spatially or topically related parenterally delivered sites spaced out to delivering the therapeutic agent through a specific localized volume or volumes of tissue(s). This, in preferred embodiments, may be through a multitude of hollow needles that penetrate through the skin or a series of jet injectors or for topical use or more viscous cream gel or past continuous flow/feed to a multitude of ports or pads.

In some clinical situations, both topical and parenteral methods are applicable.

For a parenteral delivery system using needles, one or more of the different needles may enter at different angles to aid retention, since these systems may be located in place for several minutes, and, ideally, several hours and days, if needed, to achieve an optimal therapeutic outcome. For most clinical applications which use a parenteral method, it is the preferred embodiment that many of the needles are oriented and penetrate in a parallel path. Alternatively, curved needles that enter in a spiral, rotating manner also offer significant retention.

In therapeutic application situations where the needle penetrates into the tissue to a distance that is a multiple of the spacing between multi-lumen individual needles that open at a comparable distance to the inter-needle spacing of the needles, this helps to ensure a uniform delivery of the therapeutic agent/s. Needles may have multiple lumens with or without grooves on the exterior of the needle to increase the area exposed and increase the therapeutic effect of each site. For example, in the delivery of a therapeutic agent to a tumor, prior imaging could determine the three-dimensional shape of the tumor in order that the array of needles when applied to the surface of the body overlays the tumor wherein the device, according to the invention, is placed directly on overlying skin for a breast tumor, or metastases in auxiliary lymph node. Alternatively, the device is placed laparoscopically on the surface of a solid tumor in the liver or in the pancreas.

Following a stroke this device could be inserted through a bur hole or through an intravascular route and deliver therapeutic agents such as IGF1, calcium channel blockers, progesterone, or other therapeutic agents directly into the ischemic area to prevent or limit the ischemic damage.

Thus, in one aspect, the present invention is directed to a multi-lumen, non-vascular catheter which provides a more uniform and, thus, more effective delivery of liquids containing drugs or therapeutic agents to a desired localized tissue or areas of local action.

The specific apparatus and method of use according to the invention varies depending on the properties of the tissues being treated and upon the properties of the therapeutic agent being delivered.

Very loose tissues, such as adipose tissue, allows fluid to flow much more rapidly through the intercellular spaces and allows of a much wider spacing of the tissue engaging members. Denser tissues will need higher pressures with lower flow rates. As well avascular tissues will require slower flow rates than highly vascular tissues to maintain the same tissue levels.

The number of lumens to be used in the invention may be varied, and preferably, in the use of a plurality of liquid conveying lumens each supplied by a single catheter, wherein the lumens are distinct and separate and independent one from another and non-communicative. The terminus of the lumens are adjacent to the catheter terminus but are axially spaced from one another.

It will be understood that a number of manufacturing techniques can be employed to form this catheter-lumen assembly, and that arrangements other than that shown herein can be employed.

Accordingly, in one aspect, the invention provides a device to deliver medication in a liquid formulation to a plurality of adjacent tissue sites of a mammal, said device comprising a plurality of tissue-engaging members for receiving said medication and operably engageable with said plurality of tissue sites; and means for supplying said tissue-engaging members with said formulation.

Preferably, the tissue-engageable members comprise a syringe needle for injecting, or In an alternative embodiment, the syringe could be replaced by a bead or other shaped tissue-engageable members that was inserted bluntly or with a trocar to allow insertion and stabilization within the tissue.

In an alternative embodiment, preferably, the tissue-engageable members comprise a formulation absorbent material for topical application of said medication.

Preferably, a plurality of medication reservoirs are available to be in communication with the tissue-engaging members. Each may have there flow rates controlled and varied through a central computer or variable speed controllers.

Alternatively, there is a common medication reservoir in communication with at least two of the tissue engaging members.

Preferably, the means for supplying the tissue-engaging members with the formulation comprises activatable plunger means.

Preferably, the means for supplying the tissue-engaging members with the formulation comprises a single pump/plunger with a controllable mechanical device to sequentially open gates to the plurality of tissue engaging member to individually control the medication dose per unit time to each individual or grouping of sites.

Preferably, the means for supplying the tissue-engaging members with the formulation comprises a multitude of individual pumps each supplying an individually controlled or globally controlled rate of therapeutic agent delivered to a plurality of tissues sites.

The inventor has discovered several pharmacological treatments that were initially ineffective, but were then made clinically effective by changing the application from systemic to local. But in some cases, especially in dense tissues, avascular areas, inaccessible areas, the improvement increased by using increasingly frequent doses (usually at increasingly smaller doses).

The inventor found that when attempting to inject Verapmil into an intra-penile plaque, there would be no flow until extremely strong hand pressure was applied to the syringe which resulted in an sudden, uncontrolled and extremely rapid emptying of the syringe as the pressure induced a rupture in the plaque. This cause a very high speed jet of liquid to rapidly rupture the substance of the plaque, causing the fluid to flow through and quickly out of the plaque and dissect to less dense tissue planes of the surrounding normal tissue which had much less resistance. As the needle pressure was removed and the needle was then moved to other regions in the plaque the same high pressure would be repeatedly be experienced until extremely high hand pressure again caused another rupture and rapid leakage of medication out of the plaque and into the surrounding healthy tissue. In contrast this invention produces a slow sustained infusion that would prevent rupture and ensure a much higher and much more even distribution of the therapeutic agent as it would be delivered at a rate to allow flow though the intercellular spaces inside the plaque to allow the bulk of the therapeutic agent to remain in the plaque to effect more even diffusion instead to the therapeutic agent flow out rapidly along lines of least resistance when the recommended injection technique was originally used.

By using ultra slow rates of volume/time infusion rates these dense regions in lesions such as a penile plaque which had previously showed no response, now had dramatically improved responses, e.g. plaque previously injected with the recommended technique of 2 ml of 2.5 mg/ml injected with a 22 gauge syringe at two week intervals for 6 weeks in the same patient that did not soften or shrink immediately began shrinking within a couple of weeks and softening using the slow sustained application described above.

In a further aspect, the invention provides, a method of administering a medicament to a plurality of distinct sites of tissue, lesion or organ comprising
  selecting said sites; and
  administering said medicament to each of said sites.

In a further aspect, the invention provides, administering said medicament in a manner selected from simultaneously, synchronously, individually in a routine or selected sequence at selected volumes and rates.

In a further aspect, the invention provides, injecting said medicament at said plurality of sites.

In a further aspect, the invention provides, effecting a scan of said tissue, lesion or organ selected from MRI, CAT, CT, ultrasound or other imaging device;
  reviewing selected desired sites from said scan; and
  administering said medicament to selected distinct depths at said selected sites.

In a further aspect, the invention provides, feeding said medicament to a plurality of suitably located adjacent syringes or catheters.

In a further aspect, the invention provides, dispensing said medicaments to said sites simultaneously, synchronously, individually in a routine or selected sequence at selected volumes and rates.

In a further aspect, the invention provides, topically administering said medicament to said sites.

This effect works well for localized tissue, localized lesions and localized pathological conditions.

The apparatus and process according to the invention is effective for topical as well as injectable administration wherein the device is applied to skin, or surgically implanted Endoscope for internal structures, tissues/tumours or lesions. Or following a stroke, or myocardial infarction this device could deliver therapeutic agent to prevent or reduce the ischemic damage.

BRIEF DESCRIPTION OF THE DRAWINGS

In order that the invention may be better understood, preferred embodiments will now be described, by way of example only, with reference to the accompanying drawings wherein.

DETAILED DESCRIPTION OF PREFERRED EMBODIMENTS

Figure 1:
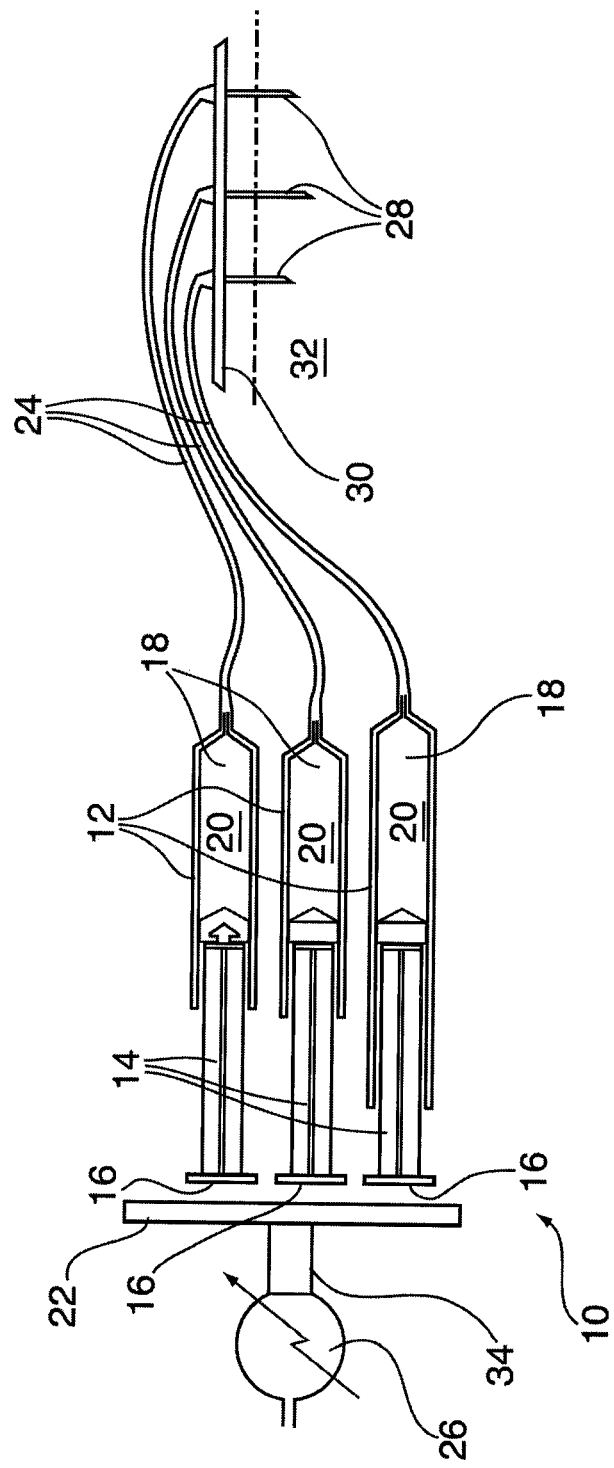
FIGS. 1 to 3 represent diagrammatic cross-sectional views of several embodiments of apparatus according to the invention.

FIG. 1 shows generally as 10 a first embodiment of a delivery system having an array of a plurality of syringes 12, three in the embodiment shown, each having a plunger 14, with head 16, movable within tube 18 operably containing medicament 20 for displacement through respective catheters 24.

Planar member 22 operably abuts head 16 under the action of variable speed pump 26 to effect displacement of plungers 14 and passage of medicament 20 through catheter or lumens 24. Each of distal ends of catheters 24 has a needle 28 retained in base 30 which penetrates tissue 32 to deliver medicament 20 at desired sites.

In the embodiment shown in FIG. 1, pump means 26 activates heads 16, simultaneously, by common flat-headed hydraulic piston 34 in abutment on heads 16.

In alternative embodiments, each syringe could be activated by its own, independent variable speed pump, hydraulic piston and head system.

In alternative embodiments, the syringes may have tubes of different volumes set by different lengths and diameters.

In further embodiments, the needle lengths may constitute a 3-dimensional array by protruding to different depths at different sites in the tissue, lesion, organ and the like.

Figure 2:
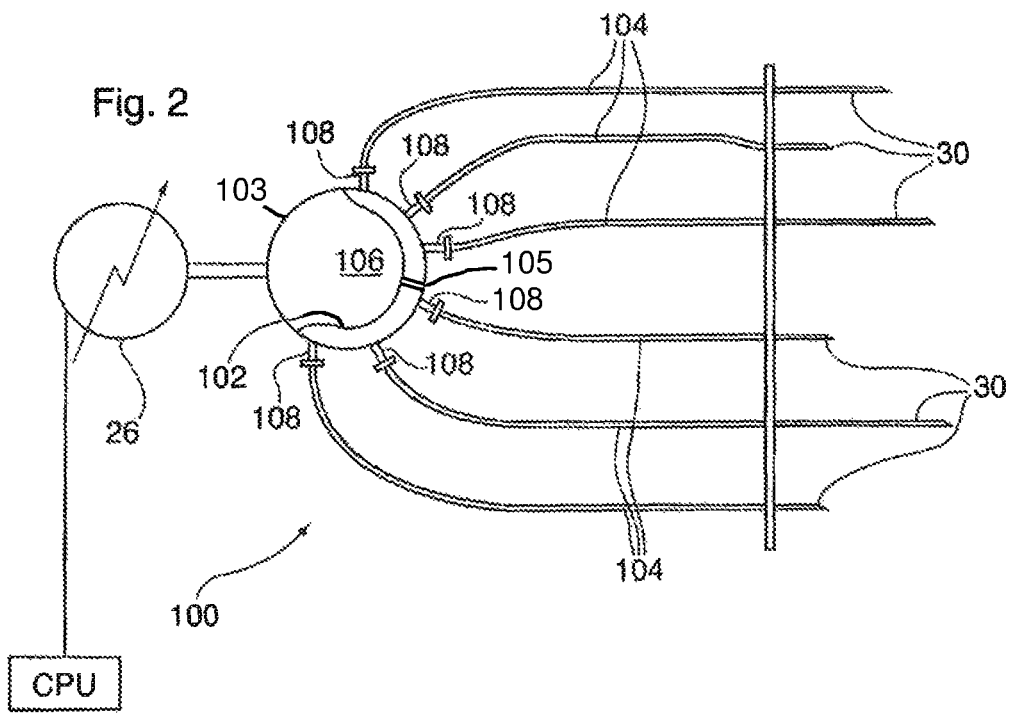

FIG. 2 shows an alternative apparatus generally as 100 which has a common circular cam 102 rotatable within a cylinder 103, which circular cam 102 is in communication, individually, with a plurality of catheters 104, each having a needle 30 at distal ends as hereinabove described with reference to FIG. 1.

A medicament is fed to a reservoir 106 on the inside of cylinder 103, and then to one or more peripheral circumferential apertures 108 by pump 26, which pump 26 is controlled by a CPU.

Rotation of circular cam 102.

Circular cam 102 is connectable to said one or more peripheral circumferential apertures 108, by which medicament is fed to catheters 104 from reservoir 106, intermittently or otherwise as desired upon rotation of cam 102.

Figure 3:
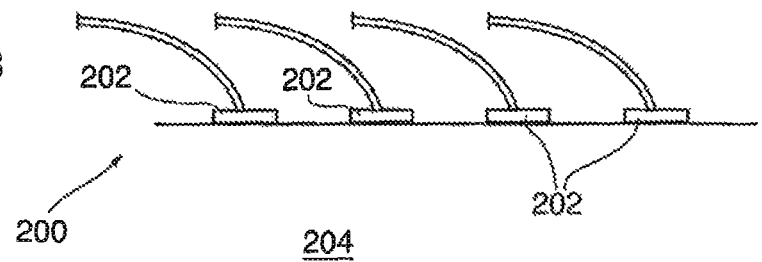

FIG. 3 shows generally as 200 an alternative embodiment in part wherein the plurality of needles 30 of FIGS. 1 and 2 have been substituted with a plurality of distant medicament-absorbent pads 202 operably contractable with the surface of tissue, lesion, organ and the like 204 for topical transfer thereto of the medicament at distinct, multiple sites.

Thus, embodiments of the invention may be used for topical or injectionable application of medicament at the surface or within a tissue, lesion, or internal organ at a steady, continuous pulsable, simultaneous, synchronous or intermittent rate of administration manner.

Figure 4:
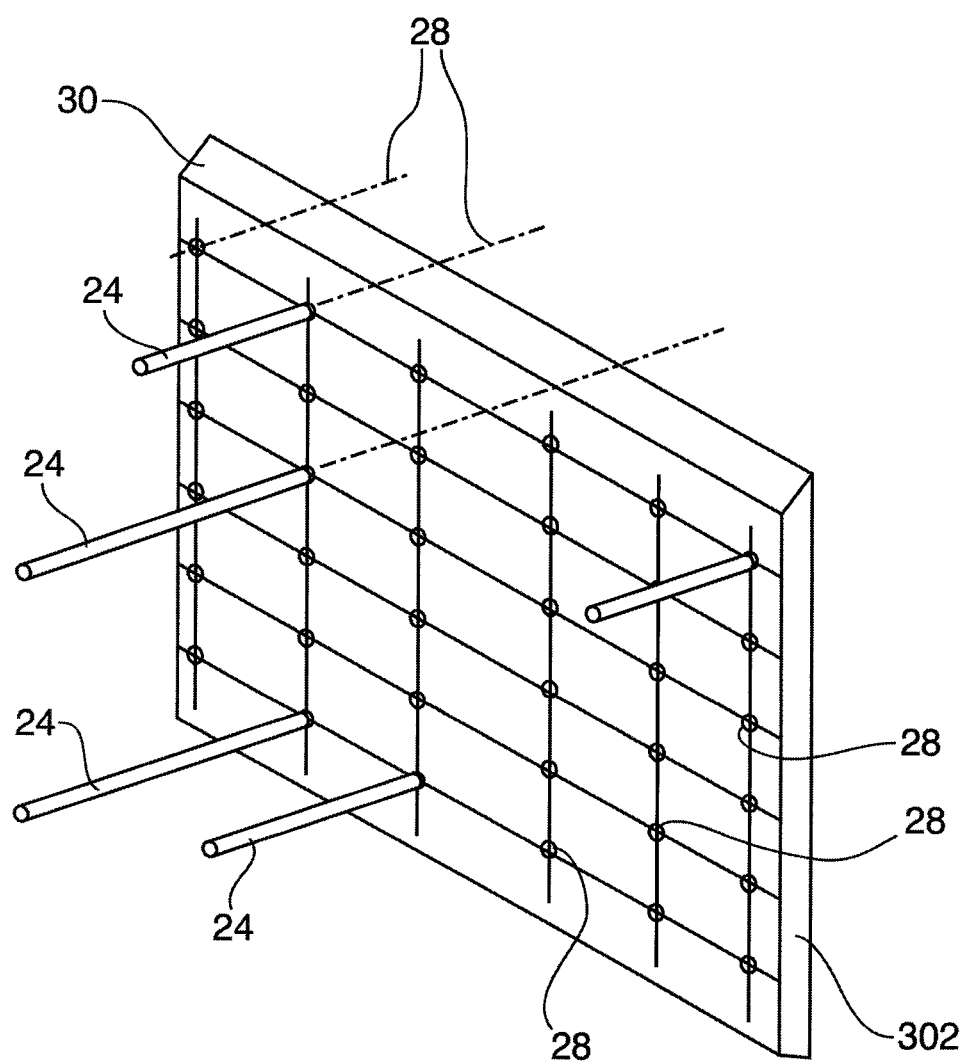
FIG. 4 is a diagrammatic perspective view of a base adapted to receive a plurality of needles; and wherein the same numerals denote like parts.

FIG. 4 shows a plurality of needles 28 or pads 202 arranged in a desired array one adjacent another at desired inter-needle/pad distances, typically on a grid network 302 of base 30. These distances may be selected, as desired, based on the nature, depth and shape of the volume of tissue, lesion and organ as determined, for example, by NMR, CAT, ultrasound and the like scans. From a reading of a scan, the aforesaid parameters of relative locations—2 or 3-dimensional positions, nature of individual administration in regard to flow rates, order sequence and the like, may be determined and selected subject to suitable software programmes electronically, and controlled most preferably, by control of the variable speed pump(s) 26.

The apparatus and method according to the invention is applicable to laparoscopic treatment of internal sites, organs and the like.

Although this disclosure has described and illustrated certain preferred embodiments of the invention, it is to be understood that the invention is not restricted to those particular embodiments. Rather, the invention includes all embodiments which are functional or mechanical equivalence of the specific embodiments and features that have been described and illustrated.

The embodiments of the invention to which an exclusive property or privilege is claimed are defined as follows:

1. A device to deliver medication in a liquid formulation to a plurality of adjacent stationary tissue sites of a mammal, said device comprising:
   a) a plurality of tissue-engaging members for receiving said medication, wherein said plurality of tissue-engaging members are operably engageable with said plurality of adjacent stationary tissue sites;
   b) a plurality of syringes containing said liquid formulation, and which syringes are separably connected to said plurality of tissue-engaging members through a plurality of flexible tubes or catheters which tubes or catheters are adapted to allow transfer of said liquid formulation from said syringes to said tissue-engaging members, wherein said flexible tubes or catheters allow the placement, angulation and depth of each of said tissue-engaging members to be individually controlled, and wherein each tissue-engaging member having an associated syringe so that the flow rate through each tissue-engaging member is separately controlled by the respective syringe; and
   c) a single activatable plunger which is configured to engage plungers of said plurality of syringes, and when activated, supplies each of said plurality of tissue-engaging members with said liquid formulation from said syringes, at a controlled or uniform rate;
   and thereby control the placement, amount and rate of medication simultaneously delivered to each of said plurality of tissue-engaging members.

2. A device as claimed in claim 1 wherein each of said plurality of tissue-engaging members comprises a needle for injecting.

3. A device as claimed in claim 1 wherein each of said plurality of tissue-engaging members comprise a formulation absorbent material for topical application of said medication.

4. The device of claim 1 wherein said syringes have different volumes.

5. A method of administering a medicament to a plurality of distinct stationary sites of tissue, lesion or organ comprising:
   providing a device as claimed in claim 1;
   selecting said plurality of distinct stationary sites;
   connecting each of said plurality of tissue-engaging members of said device, with said distinct sites; and
   administering said medicament to each of said plurality of distinct stationary sites at a uniform or controlled rate, by using said device to deliver medication in a liquid formulation.

6. A method as claimed in claim 5 comprising administering said medicament simultaneously from each syringe, at selected volumes and rates.

7. A method as claimed in claim 5 comprising injecting said medicament at said plurality of distinct stationary sites.

8. A method as claimed in claim 5 further comprising effecting a scan of distinct sites of tissue, lesion or organ using an MRI, CAT, CT or ultrasound technique;
   reviewing and selecting a desired plurality of distinct stationary sites from said scan; and
   administering said medicament to selected distinct depths at said plurality of desired distinct stationary sites.

9. A method as claimed in claim 5 comprising topically administering said medicament to said plurality of distinct stationary sites.

* * * * *